United States Patent [19]

Hayashi

[11] Patent Number: 5,114,860
[45] Date of Patent: May 19, 1992

[54] DEVICE OF MEASURING A BLOOD COAGULATING TIME

[75] Inventor: Masayoshi Hayashi, Kobe, Japan

[73] Assignee: Toa Medical Electronics Co., Ltd., Japan

[21] Appl. No.: 654,403

[22] Filed: Feb. 8, 1991

Related U.S. Application Data

[63] Continuation of Ser. No. 183,320, Apr. 6, 1988, abandoned, which is a continuation of Ser. No. 925,363, Oct. 24, 1986, abandoned, which is a continuation-in-part of Ser. No. 652,176, Sep. 18, 1984, abandoned.

[51] Int. Cl.⁵ .......................................... G01N 21/59
[52] U.S. Cl. ...................................... 436/69; 73/64.41; 356/39; 356/338; 356/341; 436/164
[58] Field of Search ............... 422/56, 68.1, 73, 82.09; 73/64.1; 436/69, 164; 356/39, 338, 341

[56] References Cited

U.S. PATENT DOCUMENTS

| | | | |
|---|---|---|---|
| 3,450,501 | 6/1969 | Oberhardt | 422/73 |
| 3,458,287 | 7/1969 | Gross et al. | 436/69 |
| 3,527,569 | 9/1970 | Mass | 422/73 |
| 3,593,568 | 7/1971 | Schmitz et al. | 436/69 |
| 3,633,012 | 1/1972 | Wilhelmson et al. | 422/55 |
| 3,658,480 | 4/1972 | Kane et al. | 422/73 |
| 3,905,769 | 9/1975 | Carroll et al. | 422/73 |
| 3,967,934 | 6/1976 | Seitz et al. | |
| 3,989,382 | 11/1976 | Kent et al. | 436/69 |
| 4,105,411 | 8/1978 | Biver | |
| 4,197,088 | 4/1980 | Meserol et al. | |
| 4,213,764 | 7/1980 | O'Connor | |
| 4,217,107 | 8/1980 | Saito et al. | 422/73 |
| 4,252,536 | 2/1981 | Kishimoto et al. | 422/73 |
| 4,454,752 | 6/1984 | Scordato | 436/69 |
| 4,497,774 | 2/1985 | Scordato | |

FOREIGN PATENT DOCUMENTS 3439344 1/1987 Fed. Rep. of Germany.

*Primary Examiner*—Timothy M. McMahon
*Attorney, Agent, or Firm*—Lucas & Just

[57] ABSTRACT

A device of measuring a blood coagulating time, the device being constructed such that when the specimen is placed in a detecting section in which it is maintained at a desired temperature, the measuring initiation time is set, followed by the transmission of a series of measuring data to a memory through an arithmetic circuit until a saturation is reached in response to which the measuring operation is stopped. On presumption that the saturating value is 100%, arithmetic operation is conducted, the results of which are stored in the remaining space of the memory. The device includes a keyboard switch whereby a time corresponding to particular percentages, such as 20%, 50%, and 80%, is previously set so as to enable the time to be easily recognized and accurately reproduced.

2 Claims, 3 Drawing Sheets

NORMAL SPECIMEN

ABNORMAL SPECIMEN

DEVICE OF MEASURING A BLOOD COAGULATING TIME

This is a continuation of /ser. No. 183,320 filed Apr. 6, 1988, which was a continuation of Ser. No. 925,363 filed Oct. 24, 1986, which was a continuation-in-part of Ser. No. 652,176 filed Sep. 18, 1984, all said prior applications being now abandoned.

BACKGROUND OF THE INVENTION

The present invention relates to a device of measuring a period of time during which blood coagulates, and more particularly, to a device of measuring a period of time required for a blood sample to coagulate, the device securing reproducibility and operational ease. Hereinafter, this period of time will be referred to as a blood coagulating time.

In general, there are many items under which ailments of animals as well as human beings are diagnosed by measuring a blood coagulating time; that is, a prothrombin time (PT), a partial thromboplastein time (PTT), a figrinogen quantity (Fbg), a deficient factor quantity, an activated partial thromboplastein time (APTT), and a Ca reapplication time. These items are decided on in accordance with the kind of a reagent to be added, and the part of the blood with which the reagent is caused to react. Take an example of a prothrombin time (PT), a systematic thromboplastein and calcium are adequately added to the plasma which was collected through centrifugal separation of blood. Subsequently, the period of time is measured until the production of whitish net-like fibrin lumps results. Let us take another example of the activated partial thromboplastein time (APTT). First, blood plasma is collected after the blood was subjected to centrifugal separation, and then acting is added thereto. In addition, calcium chloride is added. The period of time is measured until coagulation is formed More in detail, the blood plasma is stored in a refrigerator after it was obtained through centrifugal separation of blood. Acting of 0.1 ml, which was warmed in a water having a temperature of 37° C. for a minute, is poured into a test tube containing 0.1 ml of the plasma The mixture is allowed to stay in a water of 37° C. for two minutes. Then to this mixture, 0.1 ml of CaCl$_2$ of 0.02 M, which had been placed in a water having a temperature of 37° C., is added under pressure. At this moment a stop watch is switched on. The test tube is heated in the water of 37° C. for 25 seconds. The test tube is taken out, and if coagulation is observed, the stop watch is turned off. In this way the blood coagulating time is measured.

The above described practice is a hand operated direct method, which is commonly called a manual method. This manual method requires a lot of skill and experience in carrying it out. Disadvantageously, it is difficult for inexperienced persons.

To overcome this difficulty of the manual method, an automatic measuring method has been proposed An optical method is a typical example, in which blood coagulations are optically detected However, under this method the coagulations are only locally detected, which is likely to result in an inaccurate measuring of a coagulating time In addition, the reproducibility is reduced. Furthermore, under the automatic methods it is a difficult problem how to define the blood coagulating time In an optical method a particular optical level is set, and when the level is crossed, it is accepted as the blood coagulating time being completed or when a point of change (the peak value obtained by differentiating the curve of changes with time) is observed, it is recognized as the blood coagulating time.

In the level detection it is likely to happen that the previously set level is not reached when the blood sample is abnormal. In such cases it is recorded as "measuring is impossible". Referring to FIGS. 1 and 2, the level L$_3$ is set. FIG. 2 shows that the curve fails to reach the level L$_3$, thereby causing the test to continue perpetually.

Referring to FIGS. 3 and 4, in which a point of change is to be detected, if the blood sample is abnormal, the detection will be difficult. It is likely that any change is mistaken as an expected point of change though it is actually not. This is shown in FIG. 4. The data obtained by the automatic methods of the above-mentioned kinds are not necessarily in accord with those obtained by the manual direct method, and for a diagnosis purpose it is necessary to adjust the measured values by comparison with those under the conventional method.

OBJECTS AND SUMMARY OF THE INVENTION

The present invention aims at overcoming the problems and difficulties pointed out above, and has for its object to provide an improved device of measuring a blood coagulating time with high reproducibility and at ease whether the blood sample may be normal or abnormal.

Other objects and advantages of the present invention will become apparent from the detailed description given hereinafter; it should be understood, however, that the detailed description and specific embodiment are given by way of illustration only, since various changes and modifications within the spirit and scope of the invention will become apparent to those skilled in the art from this detailed description.

According to the present invention, there is provided a device of measuring a blood coagulating time, the device comprising:

a detecting section comprising an accommodater including a container containing a specimen, a cover for covering the accommodater against light, an optical unit including a source of light and a light receiver located beside the container, and a thermal controller whereby the specimen in the container is maintained at a desired temperature;

a pipette including a switch whereby the measuring of the blood coagulating time is started, wherein the switch is turned on when the specimen is placed in the container;

a detector circuit for detecting signals transmitted from the detecting section a keyboard switch by which the items to be measured and the desired conditions are input;

an arithmetic circuit connected to the pipette, the keyboard switch, the detector circuit, and the thermal controller;

a memory circuit connected to the arithmetic circuit;

a display connected to the arithmetic circuit; and a recording section connected to the arithmetic circuit, thereby ensuring that the values obtained at the detecting section are stored in the memory through the detector circuit and the arithmetic circuit until the saturation is reached with the varying values becoming constant where the arithmetic circuit transmits a signal to the detector circuit so as to stop the measuring, and conducts an arithmetic operation on presumption that the saturating value is 100%, so as to measure the blood coagulating time by comparison with the value predetermined by the keyboard switch.

DETAILED DESCRIPTION OF THE PREFERRED EMBODIMENT

Figure 1:
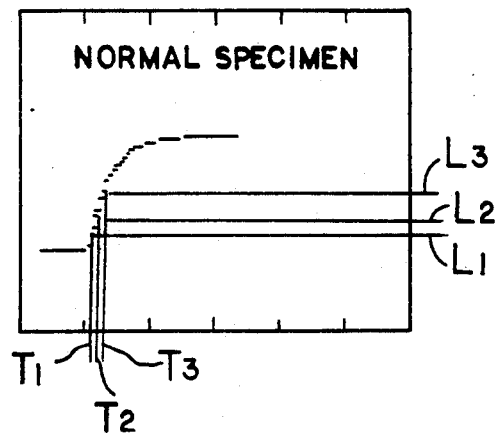
FIG. 1 is a graph obtained under the conventional level-inspection method, wherein the specimen is normal.
Figure 2:
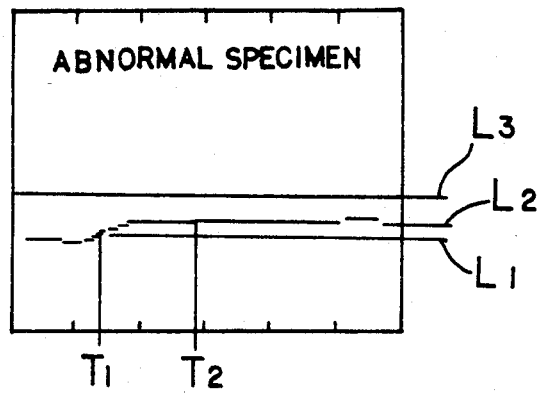
FIG. 2 is a graph obtained in the same manner as in FIG. 1, wherein the specimen is abnormal.
Figure 3:
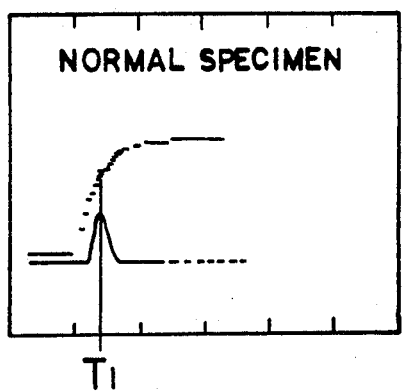
FIG. 3 is a graph obtained under the conventional point-of-change method, wherein the specimen is normal.
Figure 4:
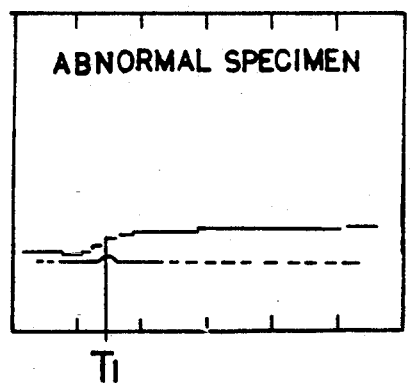
FIG. 4 is a graph obtained in the same manner as in FIG. 3, wherein the specimen is abnormal.
Figure 5:
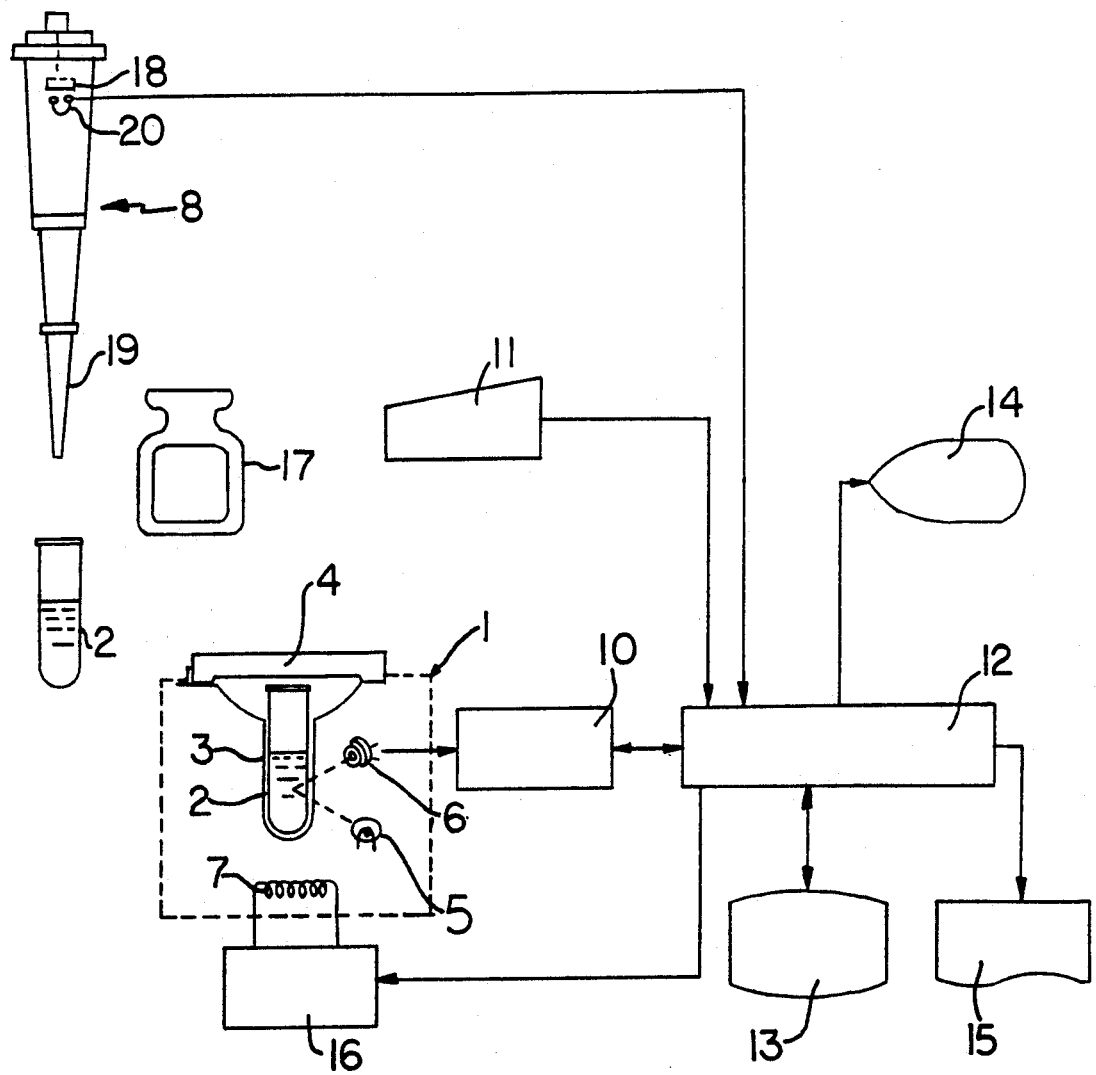
FIG. 5 is a block diagram exemplifying the structure of the device according to the present invention.

Referring to FIG. 5, there is provided a detecting section 1, which includes an accommodator 3 for accommodating a container 2 in which the specimen is stored, a cover 4 for covering the accommodator 3 against light, an optical unit including a source of light 5 and a light receiver 6, and a thermal controlling element 7 whereby the specimen in the container 2 is maintained at a desired temperature The reference numeral 8 denotes a pipette equipped with a switch which is turned on when the specimen previously warmed to a desired temperature is poured into the container 2 through the pipette 8, thereby generating a signal with which the measuring is initiated. The light receiver 6 is connected to a detector circuit 10 which is to detect signals from the detecting section 1.

There is provided a keyboard switch 11 which is to input the items to be measured and the desired conditions. The reference numeral 12 denotes an arithmetic circuit connected to the keyboard switch 11, the pipette 8, the detector circuit 10 and the thermal controlling element 7. The reference numerals 13, 14 and 15 denote a memory, a display and a recorder, respectively, all of which are connected to the arithmetic circuit 12. The reference numerals 16 and 17 denote a thermal controlling circuit and a container for containing a reagent, respectively.

The pipette 8 is provided with an upper button 18 which, when pressed down, causes a predetermined amount of liquid to drop through a lower tip 19. At the same time a switch 20 is closed, thereby transmitting a contact signal to the arithmetic circuit 12. The pipette 8 is a type available in the market.

Under the system described above a specimen previously warmed to a desired temperature and a reagent equally warmed are poured into the container 2 through the pipette 8. At this moment the switch attached to the pipette 8 is turned on so as to set a starting time for measuring the blood coagulating time at the arithmetic circuit 12. When the cover 4 is closed, the measuring is started. The measured values are transmitted in series to the detector circuit 10, to the arithmetic circuit 12, and stored in the memory 13. The measured values can be monitored through the display 14. The curves continue for some time, and then become flat, which means that a saturation is reached with the varying values becoming constant. At this stage, the arithmetic circuit 12 instructs the detector circuit 10 so as to stop the measuring, which is displayed through the display 14. The final measured value, i.e. the saturating value, is presumed to be 100% on the basis of which arithmetic operation is carried out at the arithmetic circuit 12. The results of the arithmetic operation are stored in the remaining space in the memory 13. If a time corresponding to 20%, 50% and 80% is previously set by the keyboard switch 11 such that it is printed or displayed as a final value, the time is calculated by the arithmetic circuit 12.

Figure 6:
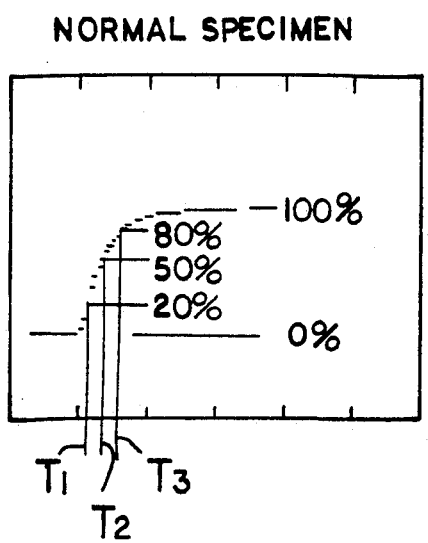
FIG. 6 is a graph exemplifying the principle underlying the present invention, wherein the specimen is normal.
Figure 7:
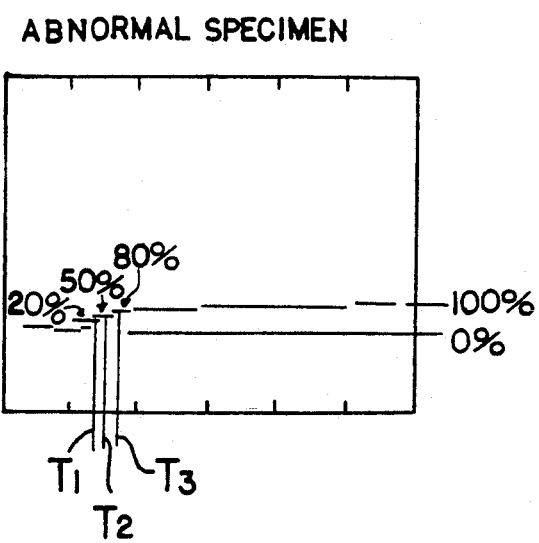
FIG. 7 is a graph depicted in the same manner as in FIG. 6, wherein the specimen is abnormal.

Under the system of the present invention it is easy to calculate the time, whether the specimen may be normal (in the case of FIG. 6) or abnormal (in the case of FIG. 7). As shown in FIGS. 6 and 7, the time corresponding to 20%, 50% and 80% can be calculated at ease. The value set in the neighborhood of 80% is found to be best in accord with the blood coagulating time which is measured by the conventional manual method.

The calculation based on percentage exhibits a constant value irrespective of mechanical malfunction, such as degeneration of the lamp or the light receiver, or an inadequate adjustment of the device, thereby ensuring that a constant value is always output.

What is claimed is:

1. A device for measuring blood coagulating time comprising:

a detecting section for measuring coagulation of blood, said detecting section comprising an accommodator for housing a container containing a specimen of blood plasma, a cover for covering the accommodator against outside light , an optical unit for continuously measuring coagulation of said specimen of blood plasma and continuously generating first output signals which are transmitted from said detecting section, said optical unit including a source of light and a light receiver located beside the container and a thermal controller whereby the specimen in the container is maintained at a desired temperature;

a pipette including a switch whereby the measuring of time for the specimen of blood to coagulate is started by activating said switch;

a detector means for receiving the first output signals from the detecting section and generating second output signals;

a keyboard switch by which items to be measured and desired conditions are input to said device;

an arithmetic means for comparing successive second output signals from said detector means, said arithmetic means connected to the pipette, the keyboard switch, the detector means, and the thermal controller;

a memory means for storing second output signals, said memory means connected to the arithmetic means;

a display screen means connected to he arithmetic means, said display screen means for generating in-process graphs of coagulation measurements; and a recording section connected to the arithmetic means, said arithmetic means connected to said pipette such that when said switch in said pipette is turned on a signal is sent to said arithmetic means to start timing a blood coagulating time, said arithmetic means connected to said detector means such that second output signals are continuously transmitted to said arithmetic means and stored in said memory means, said arithmetic means comparing each successive second output signal, transmitting a signal to the detector means so as to stop the measuring of blood coagulation when a saturation value is reached, the saturation value being obtained when said second output signals from the detector means remain constant, and said arithmetic means conducting an arithmetic operation on a presumption that the saturation value is 100% thereby determining blood coagulating time by calculating a percentage between 20% and 80% predetermined by the keyboard switch.

2. A method for measuring blood coagulation time comprising the steps of:
(a) combining blood plasma and a reagent in a container by means of a pipette, said pipette having a switch such that when the blood plasma and reagent are combined. the measuring of time for blood coagulation time starts;
(b) closing a cover on the container thereby covering the container against outside light;
(c) directing a light from a source of light through the combined blood plasma and reagent to a light receiver;
(d) generating output signals form said light reciter and feeding the signal to an arithmetic means;
(e) comparing successive output signals received by the arithmetic means;
(f) generating in-process graphs of said output signals with a display screen means;
(g) designating the output signal obtained in step (e) as a saturated value when said arithmetic means determines that successive output signals remain constant; and
(h) designating the blood coagulating time as a period of time from when the blood plasma and reagent are combined until a predetermined percentage between 20% and 80% of the saturated value is obtained.

* * * * *

UNITED STATES PATENT AND TRADEMARK OFFICE
CERTIFICATE OF CORRECTION

PATENT NO.  : 5,114,860
DATED       : May 19, 1992
INVENTOR(S) : Masayoshi Hayashi It is certified that error appears in the above-identified patent and that said Letters Patent is hereby corrected as shown below:

Column 1, line 5, change "/ser." to --Ser.--.

Column 1, line 37, change "acting" to --actin--.

Column 1, line 39, after "formed" insert --,--.

Column 1, line 41, change "Acting" to --Actin--.

Column 1, line 44, after "plasma" insert --,--.

Column 1, line 59, after "proposed" insert --,--.

Column 1, line 61, after "detected" insert --,--.

Column 1, line 64, after "time" insert --,--.

Column 1, line 67, after "time" insert --,--.

Column 2, line 43, change "accommodater" to --accommodator--.

Column 2, line 45, change "accommodater" to --accommodator--.

Column 2, line 55, after "section" insert --;--.

Column 3, line 36, after "temperature" insert --,--.

UNITED STATES PATENT AND TRADEMARK OFFICE
CERTIFICATE OF CORRECTION

PATENT NO. : 5,114,860
DATED : May 19, 1992
INVENTOR(S) : Masayoshi Hayashi

It is certified that error appears in the above-identified patent and that said Letters Patent is hereby corrected as shown below:

Column 4, line 62, change "he" to --the--.

Column 6, line 8, change "form" to --from--; and change "reciter" to --receiver--.

Signed and Sealed this

Twentieth Day of July, 1993

Attest:

MICHAEL K. KIRK

Attesting Officer

Acting Commissioner of Patents and Trademarks